(12) United States Patent
Son et al.

(10) Patent No.: US 8,292,833 B2
(45) Date of Patent: Oct. 23, 2012

(54) FINGER MOTION DETECTING APPARATUS AND METHOD

(75) Inventors: Yong-Ki Son, Daejeon (KR); Bae-Sun Kim, Daejeon (KR); Dong-Woo Lee, Daejeon (KR); Jeong-Mook Lim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 162 days.

(21) Appl. No.: 12/840,761

(22) Filed: Jul. 21, 2010

(65) Prior Publication Data

US 2011/0054360 A1    Mar. 3, 2011

(30) Foreign Application Priority Data

Aug. 27, 2009   (KR) .......................... 10-2009-0079964
Mar. 30, 2010   (KR) .......................... 10-2010-0028467

(51) Int. Cl.
    *A61B 5/103*       (2006.01)
    *A61B 5/11*         (2006.01)
    *G06F 3/033*       (2006.01)
    *G01B 17/00*      (2006.01)

(52) U.S. Cl. ..... 600/595; 600/407; 600/587; 250/316.1; 345/158; 702/40; 702/135

(58) Field of Classification Search .................. 345/158; 600/437, 595, 407, 587; 250/40, 135; 702/40, 702/135
See application file for complete search history.

(56) References Cited

U.S. PATENT DOCUMENTS

| | | | | |
|---|---|---|---|---|
| 4,662,380 A * | 5/1987 | Riley | .............................. | 600/443 |
| 4,733,668 A * | 3/1988 | Torrence | ......................... | 600/437 |
| 5,368,042 A * | 11/1994 | O'Neal et al. | .................. | 600/546 |
| 5,515,858 A * | 5/1996 | Myllymaki | .................... | 600/301 |
| 5,818,359 A * | 10/1998 | Beach | .............................. | 341/21 |
| 5,924,999 A * | 7/1999 | Agee et al. | ..................... | 600/587 |
| 6,042,555 A * | 3/2000 | Kramer et al. | ................ | 600/595 |
| 6,097,374 A * | 8/2000 | Howard | ......................... | 345/168 |
| 6,283,917 B1 * | 9/2001 | Jago et al. | ...................... | 600/437 |
| 6,413,229 B1 * | 7/2002 | Kramer et al. | ................ | 600/595 |
| 6,510,346 B2 * | 1/2003 | Gordon | ........................... | 607/100 |
| 6,716,412 B2 * | 4/2004 | Unger | ........................... | 424/9.52 |
| 6,747,632 B2 * | 6/2004 | Howard | ......................... | 345/158 |

(Continued)

FOREIGN PATENT DOCUMENTS

JP       2008-237533      10/2008

(Continued)

*Primary Examiner* — Sean Dougherty
(74) *Attorney, Agent, or Firm* — Nelson Mullins Riley & Scarborough LLP; EuiHoon Lee, Esq.

(57) ABSTRACT

The present invention relates to a finger-motion detecting apparatus and method and includes a sensing unit to be disposed on a wrist of a subject person, said sensing unit being configured to output a measurement signal into the wrist of the subject person and to receive a reflected signal of the measurement signal according to the motion of tendons in the wrist of the subject person, a signal control unit configured to control whether the measurement signal is outputted and to adjust the measurement signal on the basis of the reflected signal, and a finger-motion recognizing unit configured to detect finger motion of the subject person from the reflected signal. According to the present invention, since a sensor capable of detecting finger motion is worn on a wrist, the problem of inconvenience in existing methods is resolved.

18 Claims, 4 Drawing Sheets

U.S. PATENT DOCUMENTS

| | | | |
|---|---|---|---|
| 6,932,772 B2 * | 8/2005 | Kan | 600/490 |
| 6,979,164 B2 * | 12/2005 | Kramer | 414/5 |
| 6,984,208 B2 * | 1/2006 | Zheng | 600/438 |
| 7,078,015 B2 * | 7/2006 | Unger | 424/9.52 |
| 7,083,572 B2 * | 8/2006 | Unger et al. | 600/458 |
| 7,167,742 B2 * | 1/2007 | Camacho et al. | 600/473 |
| 7,303,555 B2 * | 12/2007 | Makin et al. | 606/28 |
| 7,610,080 B1 * | 10/2009 | Winchester et al. | 600/473 |
| 2002/0024500 A1 * | 2/2002 | Howard | 345/158 |
| 2002/0026121 A1 * | 2/2002 | Kan | 600/500 |
| 2002/0072786 A1 * | 6/2002 | Gordon | 607/100 |
| 2003/0144088 A1 * | 7/2003 | Shoane | 473/405 |
| 2004/0024312 A1 * | 2/2004 | Zheng | 600/437 |
| 2007/0118046 A1 * | 5/2007 | Turner et al. | 600/553 |
| 2008/0009736 A1 * | 1/2008 | Amadio et al. | 600/453 |
| 2010/0066664 A1 * | 3/2010 | Son et al. | 345/156 |
| 2010/0204607 A1 * | 8/2010 | Turner et al. | 600/553 |
| 2011/0054360 A1 * | 3/2011 | Son et al. | 600/595 |
| 2011/0148568 A1 * | 6/2011 | Lim et al. | 340/4.31 |
| 2011/0276282 A1 * | 11/2011 | Vanderby et al. | 702/56 |

FOREIGN PATENT DOCUMENTS

| | | |
|---|---|---|
| KR | 10-0680023 | 2/2007 |
| KR | 1020090034642 | 4/2009 |
| KR | 10-0897526 | 5/2009 |
| WO | WO 03023755 A1 * | 3/2003 |

* cited by examiner

FINGER MOTION DETECTING APPARATUS AND METHOD

CROSS REFERENCE TO RELATED APPLICATIONS

This application claims priority to Korean Patent Application No. 10-2009-0079964 filed on Aug. 27, 2009 and Korean Patent Application No. 10-2010-0028467 filed on Mar. 30, 2010, the entire contents of which are herein incorporated by reference.

BACKGROUND OF THE INVENTION

1. Field of the Invention

The present invention relates to a finger-motion detecting apparatus and method, and in particular, a finger-motion detecting apparatus and method which detects finger motion by measuring, as a reflected signal of a measurement signal, a change in the carpal tunnel of a wrist, in which a finger flexor tendons controlling finger motion exist.

2. Description of the Related Art

With recent advances in information technology, various user interface schemes have been developed to use computers using new input modals such as voice, multi-touch, and gestures, which are different from existing methods such as mouses and keyboards.

In particular, there have been many attempts to detect a motion of a hand or finger according to user's intentions in order to apply it as a user interface, and even now, researches in various fields are being conducted.

As representative examples of such technology, there are LightGlove, which has an image acquiring device such as an image sensor and an infrared emission unit that is worn on the palm side of a wrist, and detects finger motion by acquiring infrared images reflected from fingers, and Scurry, which is a watch-shaped device and ring devices including acceleration sensors worn on a wrist and fingers, respectively, and detects finger motion. Also, there are Kitty, which uses a sensing device having a conducting wire shape wound around a hand to detect finger motion by touch between fingers, and a finger motion method using an EMG. In addition, there is Gesture-Wrist, which can recognize hand gestures but not finger motion.

However, the above-mentioned existing technology should attach a device on a palm or fingers due to a signal detection structure. For this reason, user's activities are limited and it is inconvenient for a user to live in daily life while wearing a device.

SUMMARY OF THE INVENTION

Accordingly, it is an object of the present invention to provide a finger-motion detecting apparatus and method which detects finger motion by measuring a change in a carpal tunnel of a wrist, in which a finger flexor tendons controlling finger motion exists, as a reflected signal of a measurement signal such as an optical or ultrasonic wave signal.

It is another object of the present invention to suggest various examples, that control various apparatus by finger motion only and use a computer user interface as a hand motion for determine the start and end of a hand gesture in a user interface using hand gestures by additionally using an acceleration sensor or a gyro sensor.

According to an aspect of the present invention, it is provided a finger-motion detecting apparatus including: a sensing unit to be disposed on a wrist of a subject person, said sensing unit being configured to output a measurement signal into the wrist of the subject person and to receive a reflected signal of the measurement signal according to the motion of tendons in the wrist of the subject person; a signal control unit configured to control whether the measurement signal is outputted and to adjust the measurement signal on the basis of the reflected signal; and a finger-motion recognizing unit configured to detect finger motion of the subject person from the reflected signal.

The sensing unit may output the measurement signal to a carpal tunnel containing the tendons controlling the motion of fingers.

The signal control unit may adjust at least one of the strength of a signal output, the frequency of a signal output, a signal output time point, and a signal output cycle regarding the measurement signal.

The signal control unit may sense a signal regarding the finger motion by triggering the reflected signal.

The finger-motion recognizing unit may detect the finger motion from the waveform of the signal regarding the finger motion.

The finger-motion recognizing unit may determine a time block having a time period for processing the signal regarding the finger motion and buffer the signal input until end point of the time block.

The finger-motion recognizing unit may determine the start and end of the time block in reference to time points when predetermined finger motions are sensed.

The sensing unit may further comprise an acceleration sensor or a gyro sensor configured to sense hand motion of the subject person, and the finger-motion recognizing unit may determine the start and end of the determined time block on the basis of time points when the acceleration sensor or the gyro sensor senses predetermined hand motions.

The measurement signal may have at least one form of an infrared ray, a laser, and an ultrasonic wave.

The finger-motion detecting apparatus may further include a command generating unit configured to generate a command corresponding to the finger motion.

According to another aspect of the present invention, it is provided a finger-motion detecting method including: outputting a measurement signal into a wrist of an subject person; receiving a reflected signal of the measurement signal according to the motion of tendons in the wrist of the subject person; adjusting the measurement signal on the basis of the reflected signal; and detecting finger motion of the subject person from the reflected signal during a time period when the measurement signal is output while being adjusted.

In the outputting of the measurement signal, the measurement signal may be output into the carpal tunnel containing the tendons controlling the finger motion.

In the adjusting of the measurement signal, at least one of the strength of a signal output, the frequency of a signal output, a signal output time point, and a signal output cycle regarding the measurement signal may be adjusted.

The detecting of the finger motion may further include sensing a signal regarding the finger motion by triggering the reflected signal.

In the detecting of the finger motion, the finger motion may be detected from the waveform of the signal regarding the finger motion.

The detecting of the finger motion may include determining a time block having a time period for processing the signal regarding the finger motion, and buffering the signal input until end point of the time block.

The detecting of the finger motion may further include determining the start and end of the time block in reference to time points when predetermined finger motions are sensed.

The measurement signal may be in a form of at least one of an infrared ray, a laser, and an ultrasonic wave.

The finger-motion detecting method may further include generating a command corresponding to the finger motion.

According to embodiments of the present invention, since a sensor capable of detecting finger motion is worn on a wrist, a problem of inconvenience in existing methods is resolved. Therefore, embodiments of the present invention can be used as a new interface method in a wearable computing field which requires a user to use a computer without being inconvenienced while living daily life normally, that is, being hands free without holding an apparatus.

Moreover, according to embodiments of the present invention, it is possible to easily detect the motion of each finger without requiring a separate motion sensor by measuring, as a reflected signal, a change in the carpal tunnel of a wrist, where the finger flexor tendons controlling finger motion exists.

DETAILED DESCRIPTION OF THE PREFERRED EMBODIMENTS

Embodiments of the present invention will be described hereinafter with reference to the accompanying drawings.

Figure 1:
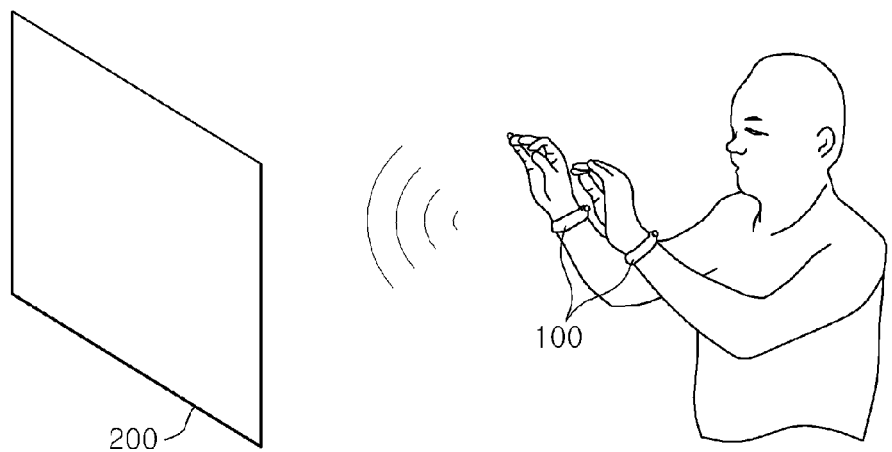
FIG. 1 is a view illustrating a system adapting a finger-motion detecting apparatus according to an embodiment of the present invention.

FIG. 1 is a view illustrating a system adapting a finger-motion detecting apparatus according to an embodiment of the present invention.

As shown in FIG. 1, a finger-motion detecting apparatus 100 according to an embodiment of the present invention is worn on a wrist of a subject person and detects finger motion on the basis of the motion of finger flexor tensions in the wrist according to the finger motion. At this time, the finger-motion detecting apparatus 100 generates a control command corresponding to the detected finger motion and transmits the control command to a control device 200 to control the operation of the control device 200.

Therefore, the subject person can control the operation of the control device 200 according to finger motion by wearing only the finger-motion detecting apparatus 100 according to the embodiment of the present invention on the wrists.

Figure 2:
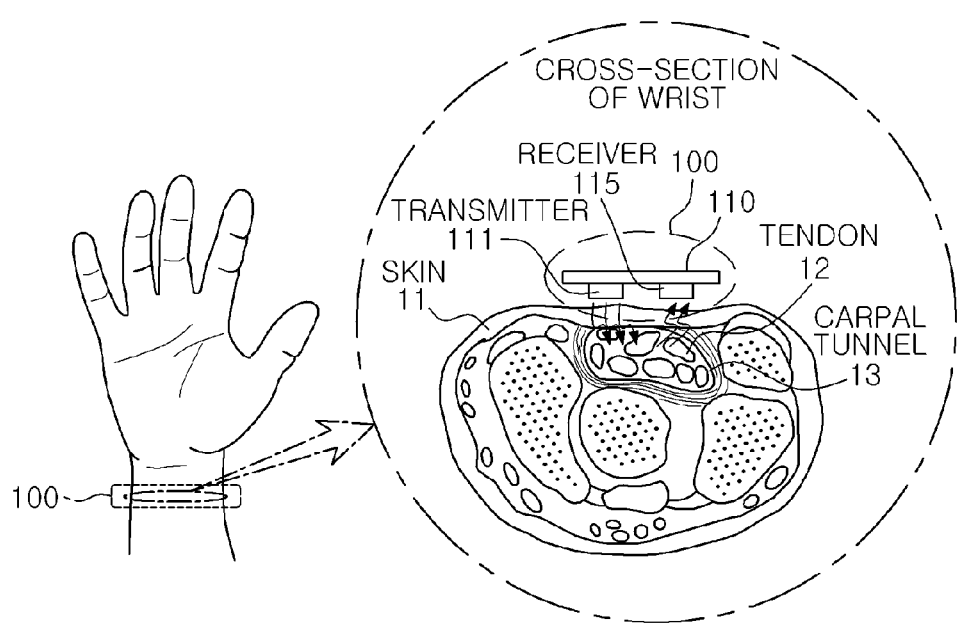
FIG. 2 is a view illustrating the principle of the finger-motion detecting apparatus according to the embodiment of the present invention.

FIG. 2 is a view illustrating the principle of the finger-motion detecting apparatus according to the embodiment of the present invention.

As shown in FIG. 2, finger flexor tendons controlling the motion of individual fingers exists in the carpal tunnel 13 of a wrist. The finger-motion detecting apparatus 100 is worn on the wrists of the subject person so that a sensing unit 110 thereof is in contact with the wrists of the subject person.

When a transmitter 111 of the sensing unit 110 outputs a measurement signal for detecting finger motion into the wrist, a receiver 115 receives a reflected signal reflected from tendons 12 in the wrist. In this way, the finger-motion detecting apparatus 100 recognizes the motion of the tendons 12 from the reflected signal and detects finger motion according to the motion of the tendons 12.

The finger-motion detecting apparatus according to the embodiment of the present invention will now be described in detail with reference to FIG. 3.

Figure 3:
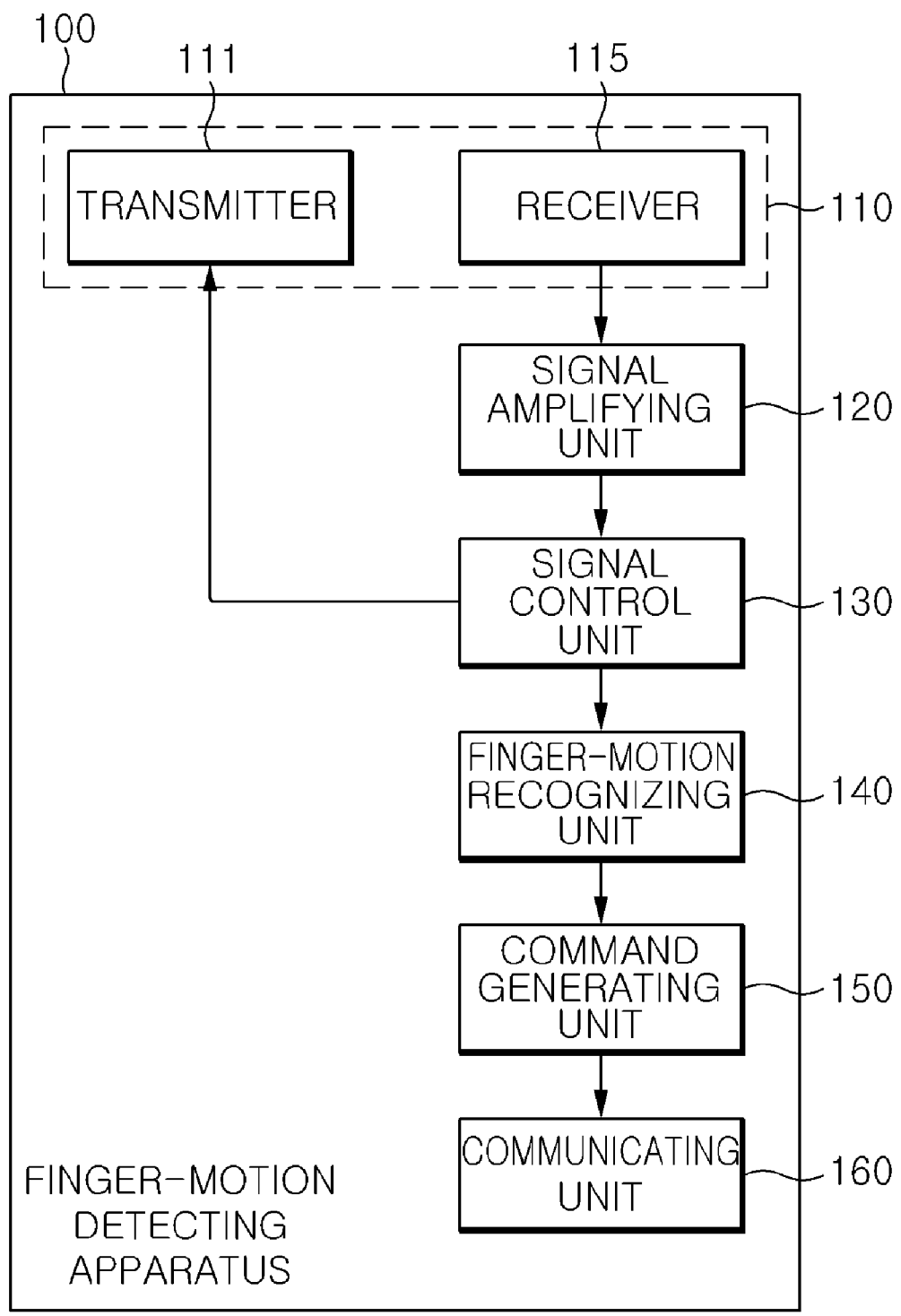
FIG. 3 is a block diagram illustrating the configuration of the finger-motion detecting apparatus according to the embodiment of the present invention.

FIG. 3 is a block diagram illustrating the configuration of the finger-motion detecting apparatus according to the embodiment of the present invention.

As shown in FIG. 3, the finger-motion detecting apparatus 100 according to the embodiment of the present invention includes a sensing unit 110, a signal amplifying unit 120, a signal control unit 130, a finger-motion recognizing unit 140, a command generating unit 150, and a communicating unit 160.

The sensing unit 110 is disposed on the wrist of the subject person, and in particular, disposed to be in contact with the skin 11 of the wrist.

The sensing unit 110 includes a transmitter 111 and a receiver 115. The transmitter 111 outputs a measurement signal into the wrist of the subject person. At this time, the transmitter 111 outputs the measurement signal to the carpal tunnel 13 which contains the tendons 12 controlling finger motion. The measurement signal is in the form of at least one of an infrared ray, a laser, and an ultrasonic wave.

The receiver 115 receives a reflected signal of the measurement reflected according to the motion of the tendons 12 in the wrist of the subject person.

The signal amplifying unit 120 amplifies the reflected signal and then transmits the reflected signal to the signal control unit 130. The signal control unit 130 controls whether the transmitter 111 outputs the measurement signal and adjusts the measurement signal on the basis of the reflected signal. At this time, the signal control unit 130 adjusts at least one of the strength of a signal output, the frequency of a signal output, a signal output time point, and a signal output cycle regarding the measurement signal to detect optimal conditions capable of sensing change of tendons 12 in the wrist.

The signal control unit 130 senses a signal regarding finger motion by triggering the reflected signal. At this time, if sensing a signal regarding finger motion greater than or equal to a reference value, the signal control unit 130 transmits the sensed signal to the finger-motion recognizing unit 140.

The finger-motion recognizing unit 140 analyzes the reflected signal to detect finger motion of the subject person. Preferably, the finger-motion recognizing unit 140 detects finger motion from the waveform of the signal regarding finger motion.

That is, the reflected signal has different waveforms according to the motion of the individual tendons 12. For this reason, the finger-motion recognizing unit 140 recognizes the motion of the individual tendons 12 from the waveform of the reflected signal and detects finger motion corresponding to the motion of a corresponding tendon 12.

Meanwhile, the finger-motion recognizing unit 140 determines the start and end of a time block in reference to a time point when signals regarding predetermined finger motions are sensed. As an example, if receiving a predetermined finger motion or a predetermined hand motion by finger motion, which indicates the start, the finger-motion recognizing unit 140 determines the start of the time block in reference to the sense time point. Moreover, if sensing predetermined finger motion or predetermined hand motion by finger motion, which indicates the end, the finger-motion recognizing unit 140 determines the end of the time block on the sense time point.

At this time, the finger-motion recognizing unit 140 buffers an input signal until end point of the time block and analyzes the signal regarding finger motion from the buffered signal.

The command generating unit 150 generates a control command corresponding to the detected finger motion. Then, the communicating unit 160 transmits the control command generated by the command generating unit 150 to the control device 200 to control the operation of the control device 200.

Another embodiment in which an acceleration sensor or a gyro sensor is added to the sensing unit 110 of the above-mentioned embodiment can be used for more various applications. In this case, finger motions can be used to make motions of pressing down and releasing such as a click and release function, which are the functions of a mouse used for a computer. It is very difficult for an operation recognition system to determine the start and end of hand gestures made in space, and the start and end of hand gestures should be determined to enable a gesture recognizing apparatus to make a correct determination. At this time, it can be applied to determine the start and end of hand gestures with motions of pressing down and releasing with a finger according to a finger-motion detecting method proposed in this specification.

The operation of an embodiment of the present invention having a configuration as described above will be described below.

Figure 4:
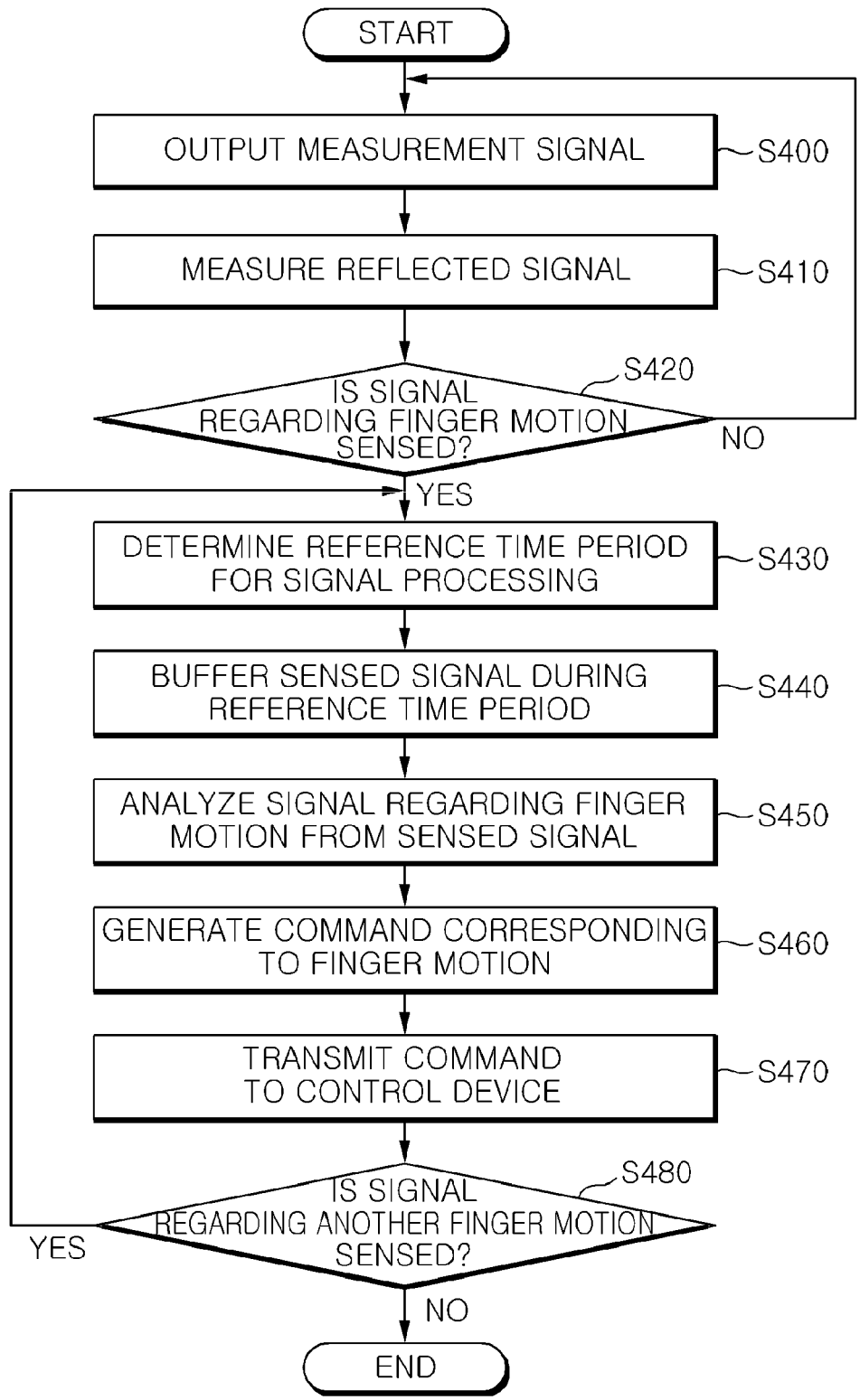
FIG. 4 is a flowchart illustrating operational steps of a finger-motion detecting method according to another embodiment of the present invention.

FIG. 4 is a flowchart illustrating operational steps of a finger-motion detecting method according to another embodiment of the present invention.

As shown in FIG. 4, the finger-motion detecting apparatus 100 outputs the measurement signal into the wrist of the subject person (S400), and then receives the reflected signal of the measurement signal according to the motion of the tendons 12 in the wrist of the subject person (S410).

At this time, the finger-motion detecting apparatus 100 outputs the measurement signal into the carpal tunnel 13 containing the tendons 12 controlling the motion of fingers. Here, the measurement signal is in the form of at least one of an infrared ray, a laser, and an ultrasonic wave.

When receiving the reflected signal, the finger-motion detecting apparatus 100 continuously outputs the measurement signal into the wrist of the subject person while adjusting the measurement signal on the basis of the reflected signal. At this time, the finger-motion detecting apparatus 100 adjusts at least one of the strength of a signal output, the frequency of a signal output, a signal output time point, and a signal output cycle regarding the measurement signal.

During a period when the finger-motion detecting apparatus 100 outputs the measurement signal while adjusting the measurement signal, it senses a signal regarding finger motion by triggering the reflected signal. If sensing a signal regarding finger motion (S420), it determines a reference time period of the time block for processing the signal regarding finger motion (S430). At this time, it determines the start and end of the time block in reference to time points when predetermined finger motions are sensed.

Next, the finger-motion detecting apparatus 100 buffers an input signal until end point of the time block determined in S430 (S440). At this time, the finger-motion detecting apparatus 100 analyzes the signal regarding finger motion on the basis of the signal buffered in S440 and detects the finger motion of the subject person from the analysis results (S450).

At this time, it may receive a signal from an acceleration sensor or a gyro sensor and detect the finger motion of the subject person on the basis of the signal input from the acceleration sensor or the gyro sensor until end point of the time block determined in S430.

Then, the finger-motion detecting apparatus 100 generates a command corresponding to the finger motion detected in S450 (S460) and transmits the command to the control device 200 to control the operation of the control device 200 (S470).

Thereafter, if sensing another finger motion (S480), S430 and subsequent steps are repeatedly performed.

Figure 5:
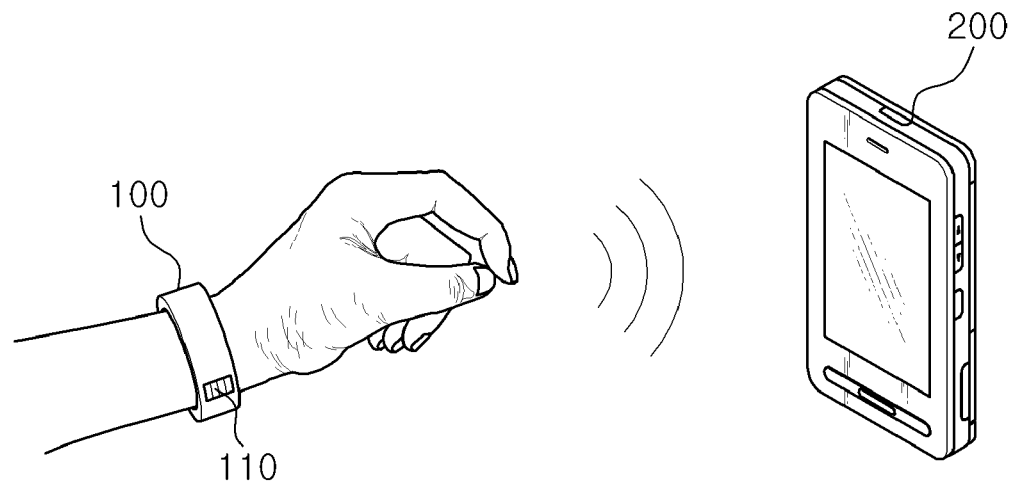
FIGS. 5 and 6 are views illustrating finger-motion detecting apparatuses according to other embodiments of the present invention.
Figure 6:
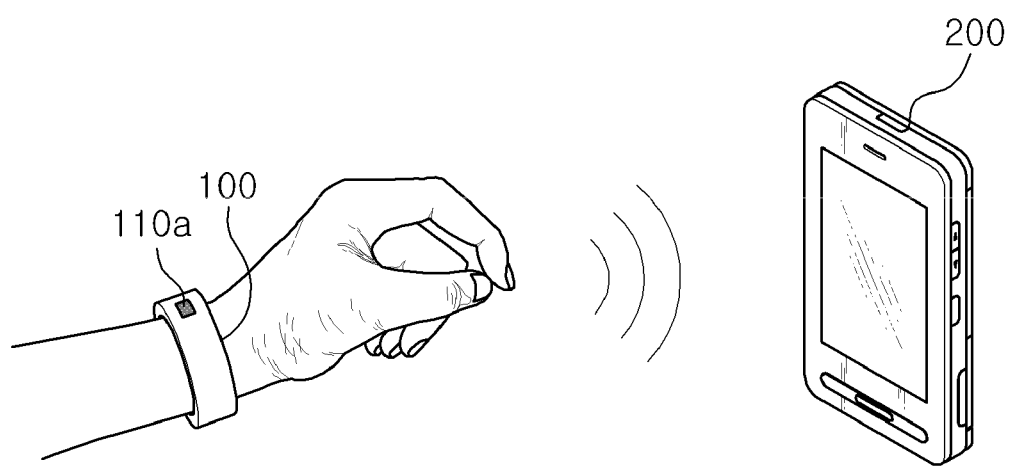

FIGS. 5 and 6 are views illustrating finger-motion detecting apparatuses according to other embodiments of the present invention.

First, FIG. 5 shows a finger-motion detecting apparatus having a plurality of sensing units as an embodiment. The embodiment of FIG. 5 has a plurality of sensing units 110 arranged in a line, making it possible to detect the motion of the tendons 12 over a wider area. Therefore, the finger-motion detecting apparatus 100 according to this embodiment can more exactly detect finger motion on the basis of reflected signals received by the plurality of sensing units 110.

Meanwhile, a control device 200 can use the finger-motion detecting apparatus 100 having the plurality of sensing units 110 as an input device. The control device 200 controls playback, a skip to the previous or next music track, volume adjustment, and the like on the basis of a control signal output from the finger-motion detecting apparatus 100.

At this time, the finger-motion detecting apparatus 100 transmits the control signal to the control device 200 in a radio communication scheme such as Bluetooth or RF.

Meanwhile, FIG. 6 shows a finger-motion detecting apparatus having an acceleration sensor or a gyro sensor capable of detecting hand motion as an embodiment.

In this case, an acceleration or gyro sensor 110a may be provided in or separately from a sensing unit 110 of the finger-motion detecting apparatus 100.

If the finger-motion recognizing unit 140 determines the time block, the acceleration or gyro sensor 110a senses hand motion until end point of the time block.

Accordingly, the finger-motion recognizing unit 140 detects the hand motion of the subject person on the basis of a signal input by the acceleration or gyro sensor 110a until end point of the determined time block.

Similarly, the finger-motion detecting apparatus 100 generates a control signal corresponding to the hand motion, and transmits the control signal to a control device 200 in a radio communication scheme such as Bluetooth or RF. The control device 200 controls playback, a skip to the previous or next music track, volume adjustment, and the like on the basis of a control signal output from the finger-motion detecting apparatus 100.

Although the finger-motion detecting apparatuses and method according to the embodiments of the present invention have been described above with reference to the accompanying drawings, they are used in a generic and descriptive sense only and not for purposes of limitation. It will be apparent to those skilled in the art that modifications and variations can be made in the present invention without deviating from the spirit or scope of the invention.

What is claimed is:

1. A finger-motion detecting apparatus comprising:
 a sensing unit to be disposed on a wrist of a subject person, said sensing unit configured to output a measurement signal which is in a form of an infrared ray into the wrist of the subject person and to receive a reflected signal of the measurement signal according to motion of tendons in the wrist of the subject person;

a signal control unit configured to control whether the measurement signal is outputted and to adjust the measurement signal to optimize conditions for sensing changes of tendons in the wrist in the reflected signal; and a finger-motion recognizing unit configured to detect finger motion of the subject person from the reflected signal.

2. The apparatus according to claim 1, wherein:
the sensing unit outputs the measurement signal to a carpal tunnel containing the tendons controlling the motion of fingers.

3. The apparatus according to claim 1, wherein:
the signal control unit adjusts at least one of a strength of a signal output, a frequency of a signal output, a signal output time point, and a signal output cycle regarding the measurement signal.

4. The apparatus according to claim 1, wherein:
the signal control unit senses a signal regarding the finger motion by triggering the reflected signal.

5. The apparatus according to claim 4, wherein:
the finger-motion recognizing unit detects the finger motion from a waveform of the signal regarding the finger motion.

6. The apparatus according to claim 4, wherein:
the finger-motion recognizing unit determines a time block having a time period for processing the signal regarding the finger motion and buffers a signal input until end point of the time block.

7. The apparatus according to claim 6, wherein:
the finger-motion recognizing unit determines a start and an end of the time block in reference to time points when predetermined finger motions are sensed.

8. The apparatus according to claim 6, wherein:
the sensing unit further comprises an acceleration sensor or a gyro sensor, and
the finger-motion recognizing unit detects hand motion of the subject person based on the signal input by the acceleration sensor or the gyro sensor until end point of the time block.

9. The apparatus according to claim 1, further comprising:
a command generating unit configured to generate a command corresponding to the finger motion.

10. A finger-motion detecting method comprising:
outputting a measurement signal which is in a form of an infrared ray into a wrist of a subject person;
receiving a reflected signal of the measurement signal according to motion of tendons in the wrist of the subject person;
adjusting the measurement signal to optimize conditions for sensing changes of tendons in the wrist in the reflected signal; and
detecting finger motion of the subject person from the reflected signal during a time period when the measurement signal is output while being adjusted.

11. The method according to claim 10, wherein:
in the outputting of the measurement signal, the measurement signal is output into a carpal tunnel containing the tendons controlling the finger motion.

12. The method according to claim 10, wherein:
in the adjusting of the measurement signal, at least one of a strength of a signal output, a frequency of a signal output, a signal output time point, and a signal output cycle regarding the measurement signal is adjusted.

13. The method according to claim 10, wherein:
the detecting of the finger motion further comprises sensing a signal regarding the finger motion by triggering the reflected signal.

14. The method according to claim 13, wherein:
in the detecting of the finger motion, the finger motion is detected from a waveform of the signal regarding the finger motion.

15. The method according to claim 13, wherein:
the detecting of the finger motion comprises
determining a time block having a time period for processing the signal regarding the finger motion, and
buffering a signal input until end point of the time block.

16. The method according to claim 15, wherein:
the detecting of the finger motion further comprises determining a start and an end of the time block in reference to time points when predetermined finger motions are sensed.

17. The method according to claim 15, further comprising:
receiving a signal from an acceleration sensor or a gyro sensor; and
detecting hand motion of the subject person based on the signal input by the acceleration sensor or the gyro sensor until end point of the time block.

18. The method according to claim 10, further comprising:
generating a command corresponding to the finger motion.

* * * * *